United States Patent
Xu et al.

(10) Patent No.: US 12,240,791 B1
(45) Date of Patent: Mar. 4, 2025

(54) PROCESS FOR SELECTIVE ETHYLENE OLIGOMERIZATION WITH ANTIFOULING COMPONENTS

(71) Applicant: Saudi Arabian Oil Company, Dhahran (SA)

(72) Inventors: Wei Xu, Thuwal (SA); Zhonglin Zhang, Dhahran (SA); Olanrewaju Malcolm Oshinowo, Dhahran (SA); Sohel Shaikh, Dhahran (SA); Motaz Khawaji, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 78 days.

(21) Appl. No.: 18/452,809

(22) Filed: Aug. 21, 2023

(51) Int. Cl.
C07C 2/32 (2006.01)

(52) U.S. Cl.
CPC ............ C07C 2/32 (2013.01); C07C 2531/22 (2013.01)

(58) Field of Classification Search
None
See application file for complete search history.

(56) References Cited

U.S. PATENT DOCUMENTS

| 3,686,350 A | 8/1972 | Yamada et al. |
| 3,879,485 A | 4/1975 | Belov et al. |

(Continued)

FOREIGN PATENT DOCUMENTS

| WO | 2013116922 A1 | 8/2013 |

OTHER PUBLICATIONS

Möller et al. ("The use of a jet loop reactor to study the effect of crystal size and the co-feeding of olefins and water on the conversion of methanol over HZSM-5", Microporous and Mesoporous Materials 29 (1999), p. 127-144). (Year: 1999).*

(Continued)

Primary Examiner — Ali Z Fadhel
(74) Attorney, Agent, or Firm — DINSMORE & SHOHL LLP

(57) ABSTRACT

A process for selectively producing oligomers may comprise bringing at least one antifouling agent into contact with a first amount of at least one aluminum alkyl compound to form at least one antifouling compound comprising the structure

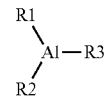

or its dimeric form; and feeding the at least one antifouling compound, an additional amount of the at least one aluminum alkyl compound, at least one titanate compound, and ethylene into a jet loop reactor and oligomerizing ethylene to produce one or more of 1-butene, 1-hexene, or 1-octene. One or more of the chemical groups R1, R2, and R3 may be the antifouling agent comprising the structure —O$((CH_2)_nO)_m$R4. n may be an integer of from 1 to 20. m may be an integer of from 1 to 100. R4 may be a hydrocarbyl group. In embodiments, the chemical groups R1, R2, or R3 that do not comprise the antifouling agent, if any, may be hydrocarbyl groups. The at least one titanate compound may be fed as a stream separate from the streams of the at least one antifouling compound and the additional amount of the at least one aluminum alkyl compound. The of the sum of the first amount and the additional amount of the at least one (Continued)

aluminum alkyl compound to the at least one titanate compound may be equal to or higher than 1.5 and equal to or lower than 3.0.

19 Claims, 6 Drawing Sheets

(56) References Cited

U.S. PATENT DOCUMENTS

| | | | |
|---|---|---|---|
| 4,101,600 A | 7/1978 | Zhukov et al. | |
| 5,811,618 A | 9/1998 | Wu | |
| 5,817,902 A * | 10/1998 | Xie | B01J 19/006 |
| | | | 585/510 |
| 5,856,612 A | 1/1999 | Araki et al. | |
| 7,297,832 B2 | 11/2007 | Blann et al. | |
| 7,300,904 B2 | 11/2007 | Dixon et al. | |
| 7,361,623 B2 | 4/2008 | Dixon et al. | |
| 7,964,763 B2 | 6/2011 | Dixon et al. | |
| 10,280,125 B2 * | 5/2019 | Sogo | C07C 2/32 |
| 10,407,358 B2 | 9/2019 | Wei et al. | |
| 10,889,533 B2 * | 1/2021 | Melibari | C07C 2/10 |
| 11,015,105 B2 | 5/2021 | Al-Yami et al. | |
| 2016/0367977 A1 | 12/2016 | Shaikh et al. | |
| 2017/0197892 A1 * | 7/2017 | Khawaji | C07C 2/32 |
| 2022/0028927 A1 | 1/2022 | Lauer et al. | |
| 2022/0280926 A1 | 9/2022 | Shaikh et al. | |

OTHER PUBLICATIONS

Notification of Transmittal of the International Search Report and the Written Opinion of the International Searching Authority, or the Declaration dated Sep. 12, 2024 pertaining to International application No. PCT/US2014/019884 filed Mar. 14, 2024, pp. 1-18.

* cited by examiner

PROCESS FOR SELECTIVE ETHYLENE OLIGOMERIZATION WITH ANTIFOULING COMPONENTS

BACKGROUND

Field

Embodiments of the present disclosure generally relate to processes and catalyst systems used in ethylene oligomerization and, more specifically, relate to processes and antifouling catalyst systems used in ethylene oligomerization which reduce undesired polymerization.

Technical Background

1-Butene and 1-hexene are important petrochemicals, especially for the productions of polyethylene. The reaction of ethylene and other alpha-olefins, especially 1-butene and 1-hexene, forms various grades of linear low density polyethylene (LLDPE), a useful commercial polymer. A source of 1-butene is the butene fraction from the effluent of a hydrocarbon cracker, such as a steam cracker or fluidized catalytic cracker. However, the process for isolating 1-butene from such an effluent requires several difficult process steps that may make the process undesirable.

Several commercial processes selectively oligomerize ethylene into alpha-olefins such as 1-butene and 1-hexene. A commercially successful dimerization process is the Alphabutol™ Process, developed by the Institute Francais du Petrole (IFP), described in A. Forestiere, et al., "Oligomerization of Monoolefins by Homogenous Catalysts", Oil & Science and Technology—Review de l'Institute Francais du Petrole, pages 663-664 (Volume 64, Number 6, November 2009). This process uses a bubble-point reactor that contains 1-butene as a process fluid to oligomerize ethylene selectively into 1-butene.

There is a known problem with oligomerization systems: polymer formation. Long residence times and poor heat removal from the highly exothermic reactions lead to the formation of polyethylene-based residues. A side effect of chronic fouling is increasingly frequent process shutdowns and higher maintenance costs for removing adhered polymer residues. Polymer residues may build layer upon layer and eventually close off openings and ports in locations with fluid flow. Additionally, a polymer coating along the wall of a reactor may act as an insulator, which may negatively affect heat transfer to the reactor system. Polymer deposits may also collect debris that can poison the reaction process.

An especially troublesome issue is the formation of "hot spots". A hot spot is an area where external cooling is ineffective and catalyst activity is high. It represents a loss of process control. A hot spot can be caused in an area of collected polymer that includes catalytically active material that fosters side-reactions, including polymerization. If left unchecked, the hot spot can eventually lead to a process shutdown due to the loss of cooling capacity, a runaway polymerization reaction, or both.

SUMMARY

There is a continual need for effective reactor systems and methods to prevent polymeric fouling on reactor system walls and tubes while maintaining the desired oligomerization rate and selectivity to form desired reaction products. Embodiments of the present disclosure meet this need by providing a process for the production of oligomers which utilizes an antifouling agent and a jet-loop reactor.

According to one embodiment, a process for selectively producing oligomers may comprise bringing at least one antifouling agent into contact with a first amount of at least one aluminum alkyl compound to form at least one antifouling compound comprising the structure:

or its dimeric form; and feeding the at least one antifouling compound, an additional amount of the at least one aluminum alkyl compound, at least one titanate compound, and ethylene into a jet loop reactor and oligomerizing ethylene to produce one or more of 1-butene, 1-hexene, or 1-octene. One or more of the chemical groups R1, R2, and R3 may be the antifouling agent comprising the structure —O$((CH_2)_nO)_m$R4. n may be an integer of from 1 to 20. m may be an integer of from 1 to 100. R4 may be a hydrocarbyl group. In embodiments, the chemical groups R1, R2, or R3 that do not comprise the antifouling agent, if any, may be hydrocarbyl groups. The at least one titanate compound may be fed as a stream separate from the streams of the at least one antifouling compound and the additional amount of the at least one aluminum alkyl compound. The of the sum of the first amount and the additional amount of the at least one aluminum alkyl compound to the at least one titanate compound may be equal to or higher than 1.5 and equal to or lower than 3.0.

Additional features and advantages of the embodiments described herein will be set forth in the detailed description which follows, and in part will be readily apparent to those skilled in the art from that description or recognized by practicing the embodiments described, including the detailed description which subsequently follows, and the claims.

DETAILED DESCRIPTION

Figure 1:
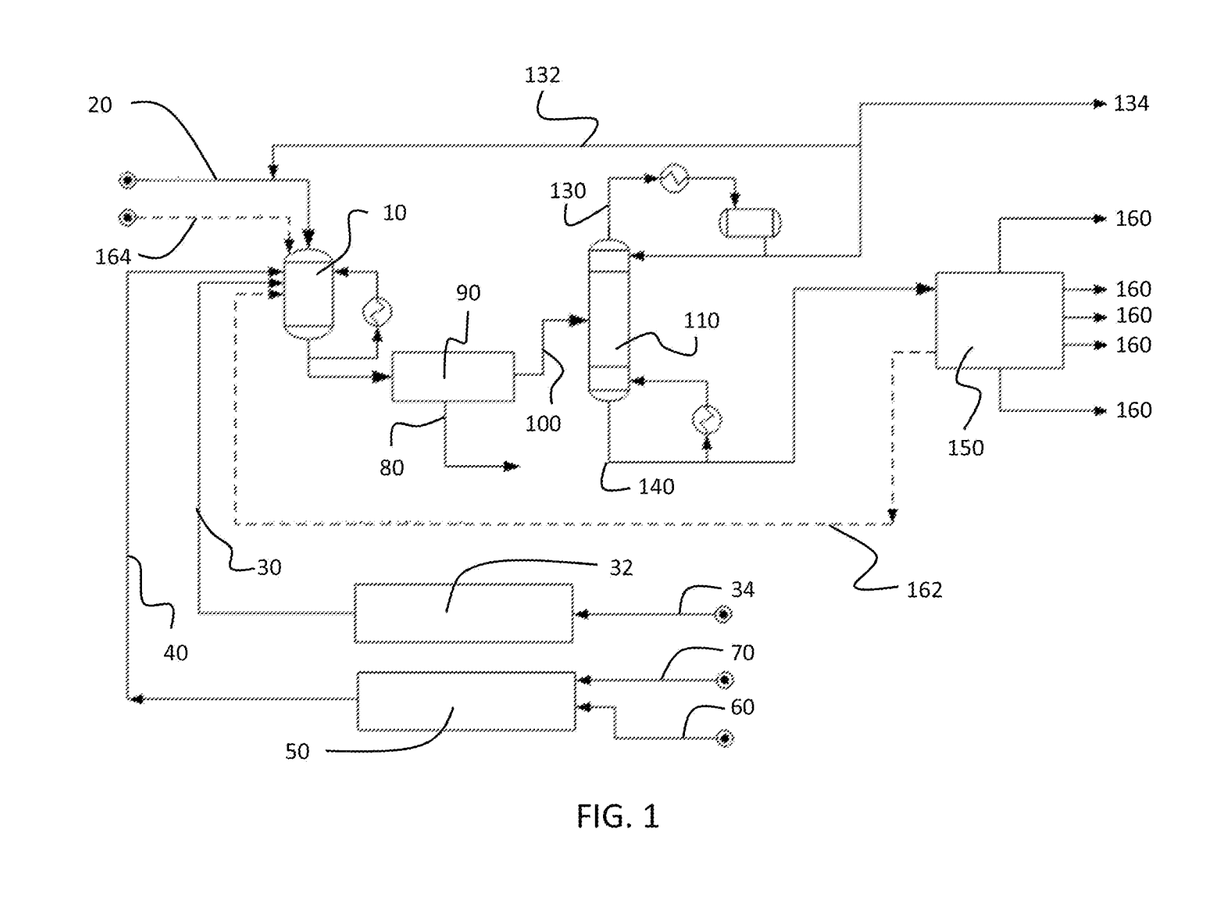
FIG. 1 is a schematic illustration of a generalized improved ethylene oligomerization process with an antifouling compound injection system in accordance with one or more embodiments of the present disclosure.

In this disclosure, the term "antifouling agent" is used to refer to agents which are added to the process, more specifically to the antifouling compound preparation section in FIG. 1, to prevent polymer fouling and to improve polymer removability.

In this disclosure, the term "antifouling compound" is used to refer to aluminum compounds which are newly formed in the antifouling compound preparation section in FIG. 1 by the reaction of the antifouling agents and aluminum alkyl compounds.

One or more embodiments of the present disclosure are directed to reactor and catalyst systems which may be utilized in promoting ethylene oligomerization, such as the dimerization of ethylene to form 1-butene, while reducing reactor fouling caused by undesired polymerization. These catalyst systems are sometimes referred to in this disclosure as "antifouling ethylene oligomerization catalyst systems" or "antifouling catalyst systems". The antifouling catalyst systems described may comprise at least one titanate compound, at least one aluminum alkyl compound, and at least one antifouling agent or derivative thereof. The antifouling catalyst systems may further comprise one or more ether compounds. The antifouling catalyst systems may be used to selectively oligomerize ethylene to produce 1-butene and other higher α-olefins, while reducing undesirable polymerization, sometimes referred to in this disclosure as "fouling". For example, reactor fouling may occur due to the formation of solid polyethylene-based residues which may reduce fluid flow and partially or fully block fluids in a reactor system from flowing at a desired rate. It should be understood that the "antifouling ethylene oligomerization catalyst systems" or "antifouling catalyst systems" described may not completely eliminate fouling during a reaction. However, these catalyst systems reduce fouling and make any formed polymer easier to remove as compared with catalyst systems which do not include an antifouling agent as described in the present disclosure. Also, it should be understood that while the catalyst systems of the present disclosure may be useful in ethylene oligomerization reactions, such as ethylene dimerization to form 1-butene, they may also be useful for the catalysis of other chemical reaction, and the antifouling catalyst systems described in this disclosure should not be considered limited in their use to the dimerization of ethylene to 1-butene.

According to embodiments of the present disclosure, 1-butene may be produced through ethylene dimerization. According to the method for 1-butene production, ethylene may be brought into contact with the antifouling catalyst system to dimerize ethylene to form 1-butene. In one or more embodiments, ethylene and an antifouling catalyst system are supplied to a reactor and mixed. The reaction may be performed as a continuous process reaction in a jet loop reactor. According to embodiments, the pressure in the reactor may be from 5 bar to 100 bar, such as from 5 bar to 80 bar, from 5 bar to 60 bar, from 5 bar to 40 bar, from 5 bar to 20 bar, from 10 bar to 100 bar, from 20 bar to 100 bar, from 40 bar to 100 bar, from 60 bar to 100 bar, from 80 bar to 100 bar, from 10 bar to 90 bar, from 20 bar to 80 bar, from 40 bar to 60 bar, or any subset thereof; and the reactor temperature may be from 30 degrees Celsius (° C.) to 180° C., such as from 50° C. to 180° C., from 75° C. to 180° C., from 100° C. to 180° C., from 125° C. to 180° C., from 150° C. to 180° C., from 30° C. to 150° C., from 30° C. to 125° C., from 30° C. to 100° C., from 30° C. to 75° C., from 50° C. to 150° C., from 75° C. to 125° C., or any subset thereof. However, process conditions outside of these ranges are contemplated, especially in view of the specific design of the reactor system and concentrations of the reactants and catalysts.

In operation an antifouling compound injection system provides an antifouling compound and a catalyst, which comprises one or more titanate compounds, to the reactor during ethylene oligomerization. The combination of the antifouling compound and the catalyst forms the antifouling catalyst system. With reference to FIG. 1, a schematic of the generalized improved ethylene oligomerization process with the antifouling compound injection system is shown. Ethylene is fed into a reactor 10 as an ethylene feed 20 where the catalyzed oligomerization of the ethylene to 1-butene and other higher α-olefins occurs. Additionally, the reactor 10 has separate inputs for a catalyst stream 30 comprising the catalyst and an antifouling compound stream 40. The antifouling compound stream 40 comprises the mixture of the at least one antifouling compound and at least one co-catalyst, which comprises at least one aluminum alkyl compound. The mixture is prepared in the antifouling compound preparation section 50 by bringing an antifouling agent provided in an antifouling agent make-up stream 60 into contact with an excess amount of the at least one co-catalyst provided in a co-catalyst make-up stream 70. The separate inputs allow interaction between the catalyst and the antifouling compound to occur within the reactor 10. Also, in other embodiments, the at least one antifouling compound and the at least one co-catalyst can be introduced to the reactor 10 as separate streams. Additionally, the catalyst stream 30 is provided to the reactor from a catalyst preparation section 32 fed from a catalyst make-up stream 34. Subsequent to the reactor 10, the spent catalyst 80 is separated from the stream exiting the reactor 10 in a catalyst removal section 90. The remaining reactor exit stream after the spent catalyst removal serves as a process stream 100 being provided to an ethylene recycle column 110. The ethylene recycle column 110 separates residual ethylene 130 from the process stream 100 for recycle as an ethylene recycle stream 132 back to the reactor 10 for oligomerization or to be purged from the and utilized as fuel system as an ethylene purge stream 134. The non-ethylene stream exiting the ethylene recycle column 110 is further provided as a product process stream 140 to a distillation section 150 for further separation of components. For example, the distillation section 150 may separate the product process stream 140 into a plurality of product streams 160 including 1-butene, 1-hexene, 1-octene, 1-decene and a heavy cut. This separation may be achieved in accordance with any standard techniques known now or in the future to one having skill in the art. For example, the ethylene oligomerization process may include a 1-butene recovery column downstream of the ethylene recycle column 110; a 1-hexene recovery column downstream of the ethylene recycle columns 110, optionally a solvent recovery column downstream of the 1-hexene recovery column, and optionally an octene recovery column downstream of the solvent recovery column. It will be appreciated that separation of the product process stream 140 into various components may be adjusted based on the make-up of the product process stream 140 and the particular chemical species or species within the product process stream 140 desired for further use or collection. The distillation section 150 may also separate solvents from the product process stream 140 which may be recycled back to the reaction 10 as a solvent recycle stream 162. Solvents may also be introduced to the reactor 10 directly with a solvent makeup stream 164.

Figure 2A:
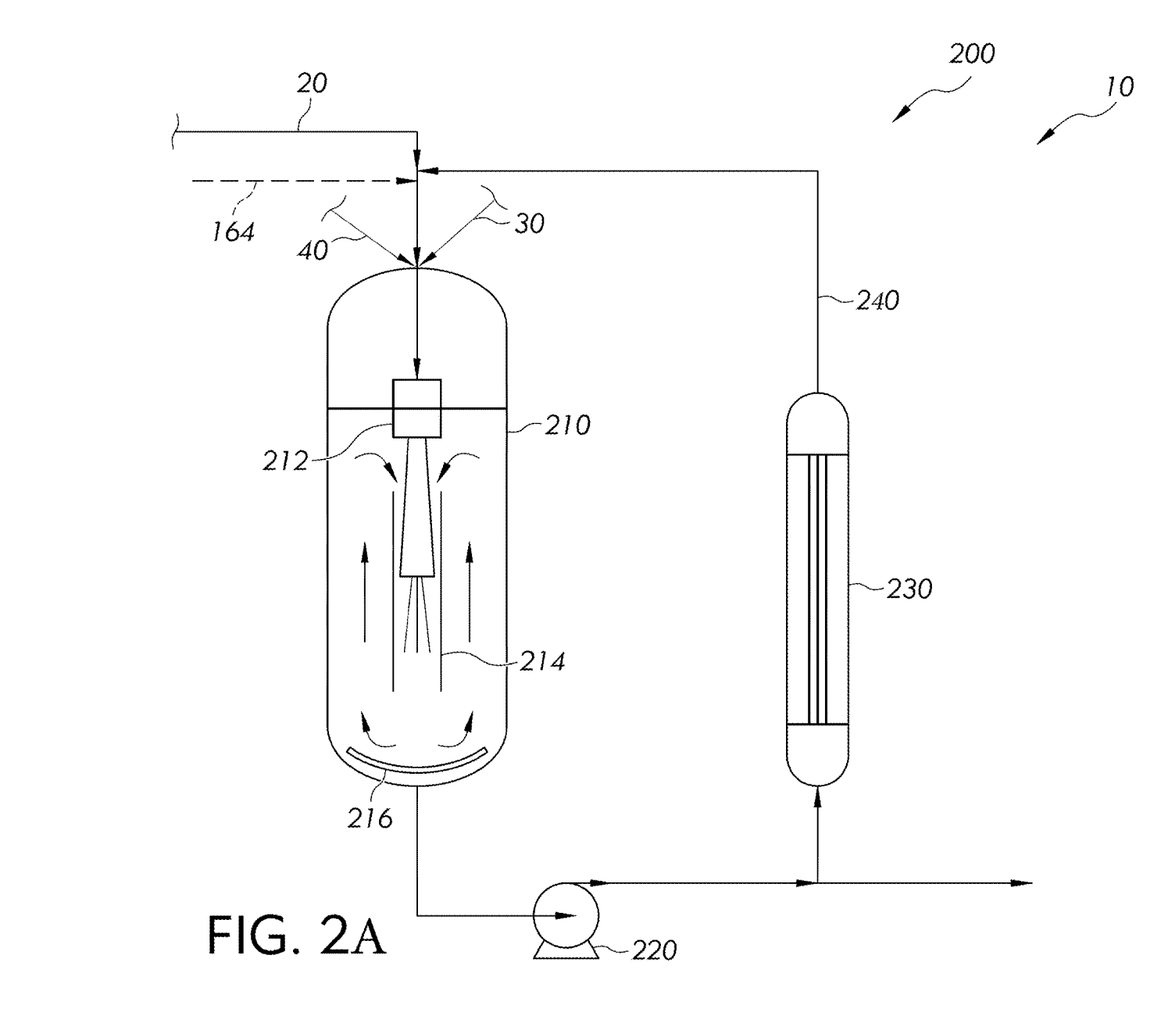
FIG. 2A is a schematic illustration of a generalized jet loop reactor in accordance with one or more embodiments of the present disclosure.

Referring now to FIG. 2A, the reactor 10 may be a jet loop reactor 200. The use of a jet loop reactor 200 is believed to reduce reactor fouling by providing increased heat transfer rates and reducing stagnant regions (which can form hot spots, which in turn can cause polymerization), relative to conventional reactors. The jet loop reactor 200 may comprise a reactor body 210. In embodiments, the jet loop reactor 200 may further comprise a recycle system including a recycle pump 220 in fluid communication with the reactor body 210 and a recycle line 240 returning the reactants to the reactor body 210. The recycle line 240 may mix the recycled reactants with the fresh reactants in the reactor inlet or upstream of the reactor inlet. A heat exchanger 230 may additionally be provided to cool the recycled reactants before reintroduction to the reactor body 210.

Figure 3A:
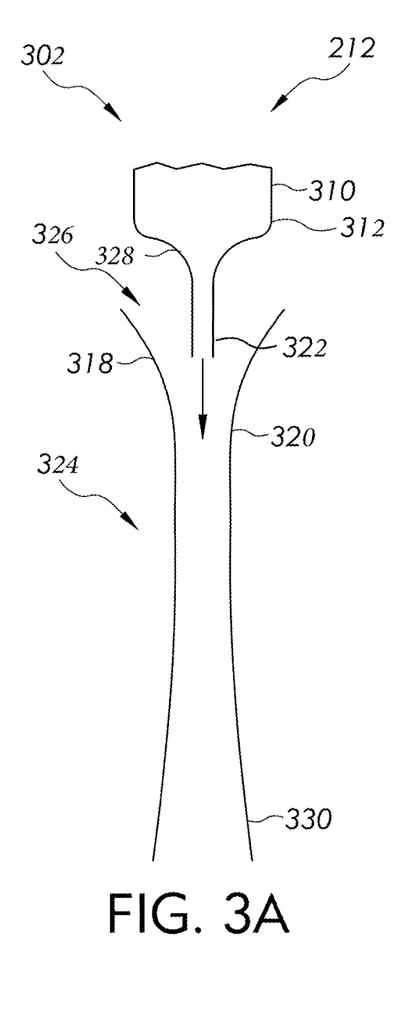
FIG. 3A is a schematic illustration of a jet nozzles in accordance with one or more embodiments of the present disclosure.
Figure 3B:
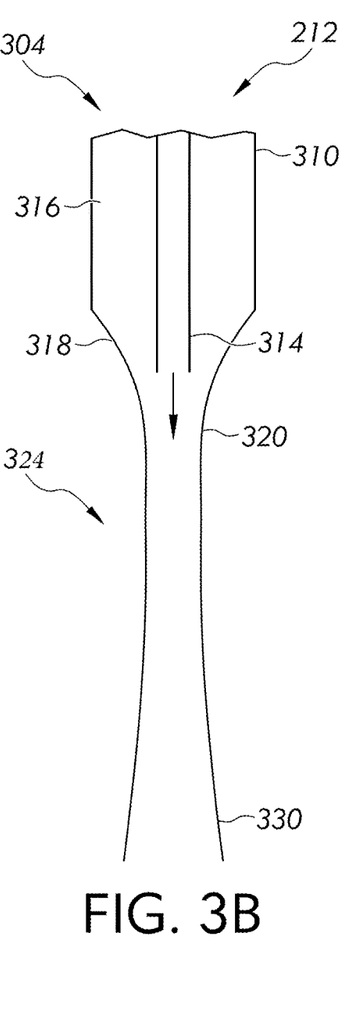
FIG. 3B is a schematic illustration of a jet nozzles in accordance with one or more embodiments of the present disclosure.
Figure 3C:
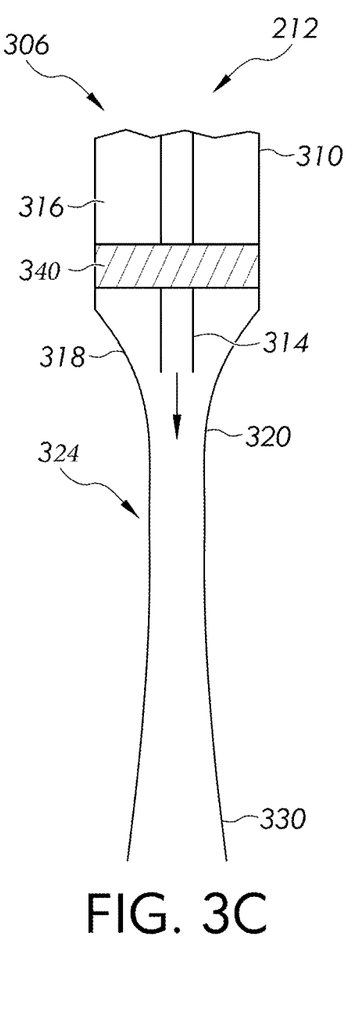
FIG. 3C is a schematic illustration of a jet nozzle in accordance with one or more embodiments of the present disclosure.

Within the reactor body 210, the jet loop reactor 200 may comprise a jet nozzle 212. All of the reactants may pass through the jet nozzle 212. The jet loop reactor 200 may be configured such that the stream of reactants passing through the jet nozzle 212 flows upward. Without being limited by theory, due to the density shift from ethylene to hexene, an upward configuration improves the reactor performance Referring now to FIGS. 3A-3C, the jet nozzle 212 may have a Venturi geometry. As depicted in FIG. 3A-FIG. 3C, the jet nozzle 212 may have an inlet 310, a throat section 320 downstream from and narrower than the inlet 310, a converging section 318 disposed between the inlet 310 and the throat section 320, and an diverging section 330 downstream from and wider than the throat section 320. The jet nozzle 212 and other aspects of the design of the jet loop reactor 200 may obviate the need for mechanical agitation and thus, in embodiments, the jet loop reactor 200 may not include a mechanical agitator.

As depicted in FIG. 3A, the jet loop nozzle 212 may be a pre-mixed open jet nozzle 302. The pre-mixed open jet nozzle 302 may comprise a mixing portion 312 upstream from an open jet first narrowing portion 328. The open jet first narrowing portion 328 may be upstream of an inlet lance 322. The inlet lance 322 may include a constant diameter section.

The pre-mixed open jet nozzle 302 may further comprise a converging-diverging section 324, downstream from and separate from the outlet. An opening 326 between the inlet lance 322 and the converging-diverging section 324 in the pre-mixed open jet nozzle 302 may allow the pre-mixed open jet nozzle 302 to entrain reactants surrounding the pre-mixed open jet nozzle 302, in addition to the fresh reactants introduced at the inlet 310. The converging-diverging section 324 may include a converging section 318, a throat section 320 downstream of the converging section 318, and a diverging section 330 downstream of the throat section 320.

As depicted in FIG. 3B, the jet loop nozzle 212 may be a closed jet nozzle 304. The closed jet nozzle 304 may comprise a main inlet portion 316 and one or more separate inlet lances 314. The separate inlet lances 314 may extend through the main inlet portion 316 until a point at or near the throat section 320. As with the pre-mixed open jet nozzle 302, the closed jet nozzle 304 may include a converging-diverging section 324 which may comprise a converging section 318, a throat section 320 downstream of the converging section 318, and a diverging section 330 downstream of the throat section 320.

As depicted in FIG. 3C, the jet loop nozzle 212 may be a closed jet nozzle with vanes 306. The closed jet nozzle with vanes 306 may have substantially the same structure as the closed jet nozzle 304 with the addition of vanes 340. The vanes 340 may cause the gasses entering the jet loop nozzle 212 to exhibit a swirling behavior in addition to their acceleration through the throat section 320. Without being bound to any particular theory, it is believed that this swirling behavior will further improve mixing of the reactants within the jet nozzle 212 and the reactor body 210.

The vanes may be positioned from 0.1 to 0.3 times the reactor inlet 310 diameter upstream of the start of the converging section 318. The closed jet nozzle with vanes 306 may have from 6 to 20 vanes, such as 6 to 16, 6 to 12, 6 to 8, 10 to 20, 14 to 20, or 18 to 20 vanes. The vanes may be canted at an angle of from 25° to 75°, such as from 25° to 50°, from 50° to 75°, from 50° to 70°, from 55° to 65°, or any subset thereof. The vanes may have a length of from 10% to 30%, such as from 10% to 25%, from 15% to 30%, from 15% to 35%, or about 20% of the inlet 310 diameter. Each of the vanes may have a thickness of from 0.1 mm to 5 mm, such as from 0.1 mm to 3 mm, from 0.1 mm to 2 mm, from 0.1 mm to 1 mm, from 0.5 mm to 5 mm, from 1 mm to 5 mm, from 0.5 mm to 1.5 mm, or about 1 mm.

For each of the jet nozzles 212 the relative dimensions are believed to control the efficiency of the nozzle. Each of the diameters described refers to the internal diameter of the specified piece of equipment.

A ratio of the internal diameter of the jet loop reactor body 210 to the inlet 310 may be from 0.1 to 2, such as from 0.25 to 2, from 0.5 to 2, from 0.1 to 1.75, from 0.1 to 1.5, from 0.25 to 1.75, from 0.5 to 1.5, from 0.75 to 1.25, or any subset thereof. In embodiments, the inlet 310 may have a diameter of from 25 mm to 75 mm, such as from 35 mm to 75 mm, from 45 mm to 75 mm, from 25 mm to 65 mm, from 25 mm to 55 mm, from 35 mm to 65 mm, from 45 mm to 55 mm, or about 50 mm.

A ratio of throat 320 diameter to inlet 310 diameter may be from 0.3 to 0.5, such as from 0.35 to 0.5, from 0.4 to 0.5, from 0.3 to 0.45, from 0.3 to 0.4, or any subset thereof.

A ratio the internal diameter of the inlet lance 314, 322 to the inlet 310 may be from 0.15 to 0.3, such as from 0.20 to 0.3, from 0.25 to 0.3, from 0.15 to 0.25, from 0.15 to 0.20, or any subset thereof.

The diverging section 330 may diverge from the throat portion 320 to the end of the nozzle at a half angle of from 2.5° to 6.5°, such as from 3.0° to 6.5°, from 3.5° to 6.5°, from 2.5° to 5.5°, from 2.5° to 4.5°, from 2.5° to 3.5°, or any subset thereof. Without being limited by theory, it is believed that half angles greater than described (such as about 6.5°) can result in flow separation and a consonant reduction in flow speed. The diverging section 330 may have a length of from 150% to 250% of the diameter of the inlet 310. In embodiments, the diverging section 330 may have a length of from 175% to 250%, from 190% to 250%, from 150% to 225%, from 150% to 210%, from 175% to 225%, from 190% to 210%, or any subset thereof of the diameter of the inlet.

The jet nozzle 212 may have an overall length 3 to 10 times the inlet 310 diameter. In embodiments, the jet nozzle 212 may have an overall length 3 to 8 times, 3 to 6 times, 3 to 5 times, 4 to 10 times, or any subset thereof the inlet 310 diameter.

Referring again to FIG. 2A, the jet loop reactor 200 may comprise a draft tube 214 disposed within a body 210 of the jet loop reactor 200. The draft tube 214 may surround (either fully or partially) at least the outlet of the jet nozzle 212. The use of a draft tube 214 may improve recirculation of the reactants within the reactor body 210. Generally, the use of a draft tube 214, in combination with the jet nozzle 212, may create a low pressure region 215 at jet nozzle 212 side of the draft tube 214. This low pressure region 215 may draw reactants back in from the body 210 of the jet loop reactor 200. It may also draw reactants up the side of the body 210 of the jet loop reactor 200, thereby creating a recirculating loop of reactants.

Figure 2B:
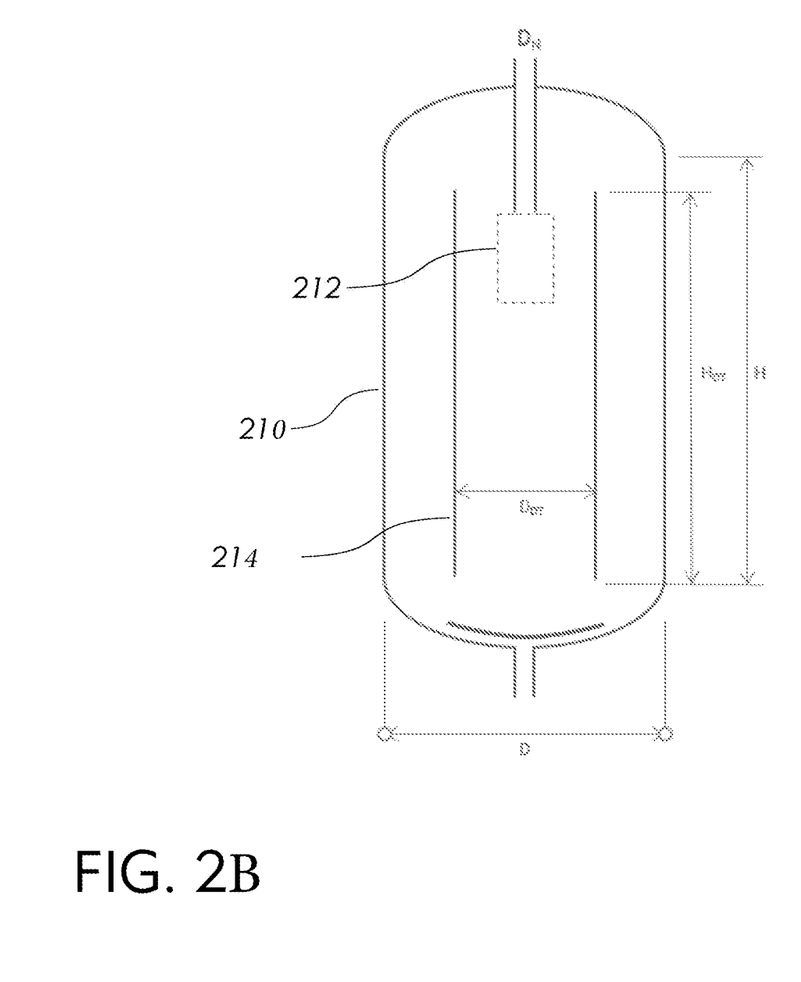
FIG. 2B is a schematic illustration of a generalized jet loop reactor in accordance with one or more embodiments of the present disclosure.

Referring now to FIG. 2B, the reactor body 210 may have an internal diameter D and a height H. The draft tube 214 may have a draft tube height $H_{DT}$ and an internal diameter $D_{DT}$. H may be from 2D to 6D, such as from 2D to 5D, from 3D to 5D, from 4D to 5D, from 2D to 4D, from 2D to 3D, from 3D to 4D, or any subset thereof. $D_{DT}$ may be from 0.2D to 0.4D, such as from 0.2D to 0.35D, from 0.2D to 0.3D, from 0.2D to 0.25D, from 0.25D to 0.4D, from 0.3D to 0.4D, from 0.35D to 0.4D, or any subset thereof. $H_{DT}$ may be from 2D to 5D, such as from 2D to 4.5D, from 2D to 4D, from 2D to 3D, from 2.5D to 5D, from 3D to 5D, from 3.5D to 5D, or any subset thereof. H—$H_{DT}$ may be from 0.2D to 0.6D, such as from 0.2D to 0.5D, from 0.2D to 0.4D, from 0.2D to 0.3D, from 0.3D to 0.6D, from 0.4D to 0.6D, from 0.5D to 0.6D or any subset thereof. The bottom of the draft tube may be 0.25D to 0.35D from the bottom of the reactor, from the deflector plate 216, or both. The top of the draft tube may be from 0.25D to 0.5D from the top of the reactor.

Referring again to FIG. 2A, the jet loop reactor 200 may further comprise a deflector plate 216. The deflector plate 216 may comprise a curved plate disposed within a direction of flow of ethylene exiting the jet nozzle 212 This deflector plate may serve to redirect the flow of reactants (such as ethylene) and cause them to recirculate within the reactor body 210.

Figure 4:
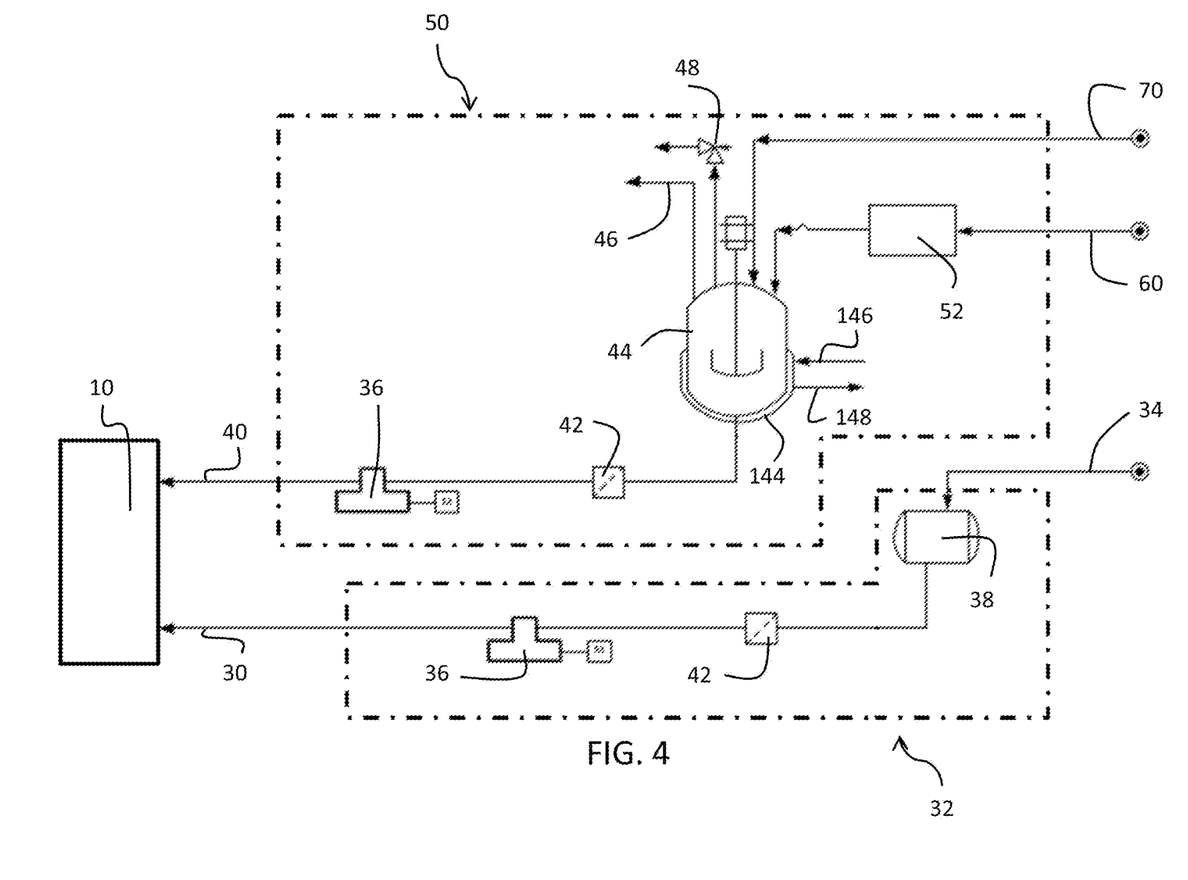
FIG. 4 is a schematic of a catalyst feed stream into a reactor and an antifouling compound feed stream into the reactor in accordance with one or more embodiments of the present disclosure.

With reference to FIG. 4, a schematic of the catalyst feed stream 30 into the reactor 10 is provided. The catalyst is provided from a catalyst source to the reactor 10 by a pump 36 or other locomotion means. In at least one embodiment, a catalyst storage drum 38 is provided which provides a reservoir of catalyst for supply to the reactor 10 on an on-demand basis. The catalyst storage drum 38 maintains a reservoir of catalyst for supply to the reactor 10 and is resupplied from the catalyst make-up feed 34. Further, in embodiments, a filter 42 is provided in-line in the conduit connecting the catalyst source or catalyst storage drum 38 to the reactor 10. The filter 42 provides removal of particulates or other foreign components from the catalyst stream. As shown in FIG. 4, the catalyst source may be a titanate complex in tetrahydrofuran (THF).

Throughout this disclosure the discussed catalyst comprises at least one titanate compound. However, it will be appreciated by one skilled in the art that other catalysts known to those skilled in the art may be equally utilized in the ethylene oligomerization reaction and the antifouling compound injection system. For example, catalyst systems based on transition metal complexes such as nickel, chromium, zirconium, or other metal complexes may be used in addition to or as a substitute for the discussed titanate compound.

With reference to FIG. 4 again, a schematic of the antifouling compound feed stream into the reactor 10 is provided. The at least one antifouling compound is formulated in an antifouling compound mixing vessel 44 and subsequently provided to the reactor 10 by a pump 36 or other locomotion means. In one or more embodiments, the at least one antifouling agent is brought into contact with an excess amount of the at least one co-catalyst in the antifouling compound mixing vessel 44 to form a mixture of the at least one antifouling compound and the remainder of the at least one co-catalyst. The reaction of the antifouling agent and co-catalyst to form the antifouling compound varies based on the specific structure of the antifouling agent. For example, when the antifouling agent is an alcohol, the reaction includes protonolysis of the alkyl group of the co-catalyst. The reaction of forming the antifouling compound from the antifouling agent and the co-catalyst may result in the formation of gas, which is vented from the antifouling compound mixing vessel 44 as an off gas stream 46. The specific gas generated for discharge as the off gas stream 46 varies depending on the structure of the co-catalyst. For example, triethylaluminum generates ethane gas during the antifouling compound formation. The resulting mixture of the antifouling compound and excess co-catalyst is provided to the reactor 10 as a separate injection from the catalyst. In other embodiments, the at least one antifouling agent is premixed with the same or a lesser amount of the at least one co-catalyst to form a mixture containing the at least one antifouling compound and no co-catalyst. Then, the resulting mixture is provided to the reactor 10 along with an additional amount of the at least one co-catalyst. Even in this case, the mixture and the co-catalyst are provided as separate streams from the catalyst. Without wishing to be bound by theory, it is believed providing of the antifouling compound, the co-catalyst, and the catalyst as a combined stream can cause undesirable increase in fouling and should be avoided.

The antifouling compound mixing vessel 44 may additionally include a cooling jacket 144 to maintain temperature control of the antifouling compound during formation from the mixing of the antifouling agent and the co-catalyst. The cooling jacket 144, in one or more embodiments, comprises water cooling with a cooling water inlet 146 and a cooling water return 148 to continually maintain the antifouling compound mixing vessel at a constant or desired temperature range. The internal temperature of the mixing vessel may be from 10° C. to 90° C.

In one or more embodiments, the antifouling compound mixing vessel 44 comprises a pressure relief valve 48. The pressure relief valve 48 is operational to allow the antifouling compound mixing vessel 44 to vent in the event of excessive pressurization. As previously discussed, the formation of the antifouling compound may result in the formation of one or more off-gases normally discharged as the off gas stream 46 which can cause over pressurization of the antifouling compound mixing vessel 44. To avoid rupture of the antifouling compound mixing vessel 44, the pressure relief valve 48 may allow quickened venting of the antifouling compound mixing vessel 44 in the event of excessive off-gas formation or insufficient off-gas collection or venting through typical means.

As commercially available antifouling agents may contain water, the antifouling agent is mixed with an alkane solvent and then optionally passed through a drying bed 52 to remove or reduce the water content in the antifouling agent in the antifouling agent make-up steam 60 before being provided to the antifouling compound mixing vessel 44. In one or more embodiments, the alkane solvent is hexane. In various other embodiments, the alkane solvent is butane, pentane, hexane, heptane, octane, and branched isomers thereof. In further embodiments, the alkane solvent is a cyclic alkane such as cyclohexane or methylcyclohexane. The water content in the antifouling agent in one or more embodiments is maintained lower than approximately 0.3 weight % (wt %) since an excessive amount of water could deactivate the antifouling catalyst system. In further embodiments, the water content in the antifouling agent is maintained lower than approximately 0.1 wt %. The drying beds 52 contain a drying agent to remove water from the antifouling agent make-up stream 60. In various embodiments the drying agent is molecular sieves or sodium (Na) supported on alumina or silica. It will be appreciated by one skilled in the art that other means of drying the antifouling agent are known and they are equally envisioned.

As described previously in this disclosure, embodiments of the described antifouling catalyst systems may comprise one or more titanate compounds. The titanate compounds serve as the catalyst. While several titanate compounds may be included in the antifouling catalyst system, in some embodiments a single titanate compound may be included in the antifouling catalyst system. In one or more embodiments, the titanate compound may be an alkyl orthotitanate. An alkyl orthotitanate has the structure $Ti(OR)_4$ in which R is independently at each occurrence a linear, branched, or cyclic alkyl group. In one or more embodiments, each alkyl group may comprise from 2 to 8 carbon atoms, where each R group may be the same or different. Suitable alkyl titanates may include tetraethyl orthotitanate, tetraisopropyl orthotitanate, tetra-n-butyl orthotitanate (sometimes referred to as titanium butoxide), and tetra-2-ethylhexyl orthotitanate. In one or more embodiments, the titanate compound of the antifouling catalyst system consists of tetra-n-butyl orthotitanate.

As also described previously in this disclosure, embodiments of the described antifouling catalyst systems may comprise one or more aluminum alkyl compounds. The aluminum alkyl compounds serve as the co-catalyst and are combined with the antifouling agent to form the antifouling compound. The aluminum alkyl compounds may have a structure of $AlR'_3$ or $AlR'_2H$, where R' is a linear, branched, or cyclic alkyl group comprising from 1 to 20 carbon atoms, or an aluminoxane structure, that is, a partial hydrolysate of trialkylaluminum compounds. It will be appreciated that each R' may be unique providing a formula of $AlR'1R'2R'3$. For example, and not by way of limitation, suitable aluminum alkyl compounds may include trialkylaluminums. The trialkylaluminums may be triethylaluminum, tripropylaluminum, triisobutylaluminum, trihexylaluminum, or trioctylaluminum. In one or more embodiments, the aluminum alkyl compound of the antifouling catalyst system consists of triethylaluminum.

Throughout this disclosure the discussed co-catalyst is an aluminum alkyl compound, and more specifically triethylaluminum (TEAL). However, it will be appreciated by one skilled in the art that other co-catalysts may be equally utilized in the formulation of the antifouling compound. For example, methylaluminoxane (MAO), trimethylaluminum, triisobutylaluminum, trioctylaluminum, or combinations thereof may be used in addition to or as a substitute for the discussed aluminum alkyl compound.

In one or more embodiments, the antifouling agent to be combined with the aluminum alkyl compound to form the antifouling compound may be selected from one or more of a phosphonium ($[R1R2R3R4P]^+$), sulfonate ($[ROSO_2]^-$), sulfonate ($[R1R2R3S]^+$), and a fouling-preventing surfactant including nonionic surfactants, anionic surfactants, cationic surfactants, and zwitterionic surfactants. Examples of nonionic surfactants include polyoxyethylene monoalkyl ethers ($CH_3(CH_2)_{3-27}(OC_2H_4)_{1-25}OH$), polyoxyethylene dialkyl ethers ($CH_3(CH_2)_{3-27}(OC_2H_4)_{1-25}O(CH_2)_{3-27}CH_3$), polyoxypropylene monoalkyl ethers ($CH_3(CH_2)_{3-29}(OC_3H_6)_{1-25}OH$), polyoxypropylene dialkyl ethers ($CH_3(CH_2)_{3-27}(OC_3H_6)_{1-250}(CH_2)_{3-27}CH_3$), polyoxyethylene-polyoxypropylene-polyoxylethylene block copolymers ($HO(C_2H_4O)_{1-25}(C_3H_6O)_{1-25}(C_2H_4O)_{1-25}H$), polyoxypropylene-polyoxyethylene-polyoxypropylene block copolymers ($HO(C_3H_6O)_{1-25}(C_2H_4O)_{1-25}(C_3H_6O)_{1-25}H$), oligoglucoside monoalkyl ethers ($CH_3(CH_2)_{3-27}(OC_6H_{10}O_5)_{1-3}OH$), polyoxyethylene mono(alkylphenyl) ethers ($CH_3(CH_2)_{3-27}(C_6H_4)(OC_2H_4)_{1-25}OH$), glycerol alkyl esters, N,N,N',N'-tetra(polyoxyalkylene)-1,2-ethylenediamines (($H(O(CH_2)_{2-3})_{1-25})_2NCH_2CH_2N(((CH_2)_{2-3}O)_{1-25}H)_2$, and polyoxyethylene sorbitan alkyl esters such as polysorbate. Examples of anionic surfactants include sodium stearate and sodium 4-(5-dodecyl) benzenesulfonate. Examples of cationic surfactants include dimethyldioctadecylammonium chloride and dimethyldioctadecylammonium bromide. Examples of zwitterionic surfactants include 3-[(3-cholamidopropyl)dimethylammonio]-1-propanesulfonate, cocamidopropyl hydroxysultaine, cocamidopropyl betaine, and phosphatidylethanolamine.

The antifouling catalyst systems may comprise one or more antifouling compounds or derivatives thereof. As used herein, a derivative refers to a derivative structure of an antifouling compound, such as a dimer, trimer, oligomer, polymer, isomer, hydrolysate of an antifouling compound described in this disclosure. It will be appreciated that differing antifouling agents will form differing antifouling compounds when combined with the aluminum alkyl compounds. In one or more embodiments, an antifouling compound may comprise a central aluminum molecule bonded to all three of a first chemical group R1, a second chemical group R2, and a third chemical group R3. Chemical Structure #1 depicts a generalized chemical structure of an antifouling compound with R1, R2, and R3 representing antifouling groups, which are derived from the antifouling agent.

Chemical Structure #1

Generalized Antifouling Compound

In one or more embodiments, one or more of R1, R2, and R3 are antifouling groups comprising the structure —O(($CH_2)_nO)_mR4$, where n is an integer of from 1 to 20. In various embodiments, n is an integer of from 1 to 10, 1 to 5, or 2 to 3, m is an integer of from 1 to 100, and R4 is a hydrocarbyl group. In various embodiments, n is an integer of from 1 to 10, 1 to 5, or 2 to 3 and m is an integer of from 1 to 50, 1 to 20, or 1 to 10. The structure of the antifouling group, —O(($CH_2)_nO)_mR4$, is depicted in Chemical Structure #2. The central aluminum atom is bonded to a terminal oxygen of the antifouling group opposite to the R4 hydrocarbyl group. As used throughout this disclosure, a hydrocarbyl group refers to a chemical group that consists of hydrogen and carbon atoms. For example, a hydrocarbyl group may be linear, branched, or cyclic, and may comprise one or more alkyl moieties, one or more alkenyl moieties, one or more alkynyl moieties, aryl moieties, or combinations thereof. In various embodiments, R4 may be a hydrocarbyl group having from 1 to 100 carbon atoms, from 2 to 50 carbon atoms, or from 8 to 28 carbon atoms.

Antifouling Group

Chemical Structure #2

As previously described in this disclosure, one, two, or all three of R1, R2, and R3 may comprise the antifouling groups comprising the structure of Chemical Structure #2. In embodiments described in this disclosure, the chemical groups R1, R2, or R3 that do not comprise the antifouling group, if any, are hydrocarbyl groups. For example, R1 may be an antifouling group with the structure depicted in Chemical Structure #2 and R2 and R3 may be hydrocarbyl groups. In another embodiment, R1 and R2 may be antifouling groups with the structure depicted in Chemical Structure #2, and R3 may be a hydrocarbyl group. In another embodiment, R1, R2, and R3 may be antifouling groups with the structure depicted in Chemical Structure #2. When at least two of R1, R2, and R3 are hydrocarbyl groups, they may be identical to one another or may be different hydrocarbyl groups. Also, when two or more of R1, R2, or R3 are antifouling groups, the antifouling groups may be identical or chemically different. However, they will each have the generic structure depicted in Chemical Structure #2. In various embodiments, R1, R2 and R3 that are hydrocarbyl groups may each have from 1 to 100 carbon atoms, from 2 to 75 carbon atoms, or from 2 to 50 carbon atoms. For example, if R1, R2, or R3 are hydrocarbyl groups, they may be linear alkyl groups such as methyl, ethyl, propyl, or butyl groups, or branched alkyl groups such as isopropyl or isobutyl groups.

By way of example, if R1 is an antifouling group, and R2 and R3 are hydrocarbyl groups, the generalized structure of the antifouling compound can be represented by Chemical Structure #3.

Chemical Structure #3

Example of Generalized Antifouling Compound

In one or more embodiments, the antifouling compound may comprise an R1 group that is an ethyl group, an R2 group that is an ethyl group, and an R3 that is an antifouling group having the structure —O((CH$_2$)$_n$O)$_m$R4, where n=2, m=4, and R4 is a dodecyl group. Such an antifouling compound can be written as (CH$_3$CH$_2$)$_2$AlO(CH$_2$CH$_2$O)$_4$(CH$_2$)$_{11}$CH$_3$, and has the chemical structure depicted in Chemical Structure #4, where "Et" represents an ethyl group.

Chemical Structure #4

Example of Antifouling Compound

In one or more embodiments, the antifouling compound may be present as a dimerized form, referred to herein as an example of a derivative of an antifouling compound. A prepared antifouling compound may be present in both dimerized and non-dimerized, that is, non-bonded, form. For example, in a dimerized state, the antifouling compound may comprise a structure as shown in Chemical Structure #5. Chemical Structure #5 shows the dimerized embodiment of the antifouling compound structure depicted in Chemical Structure #3. In a dimerized embodiment, bonds may form between the central aluminum atoms of an antifouling compound molecule and an oxygen atom of a neighboring antifouling compound molecule. It should be understood that while in Chemical Structure #5 the central aluminum atoms are bonded to the oxygen atom in the neighboring antifouling compound that is the nearest to its central aluminum atom, in other embodiments, this may not be the case, and the a central aluminum atom may bond with an oxygen atom of a neighboring antifouling compound which is not the nearest to its central aluminum atom.

Chemical Structure #5

Example of Dimerized Antifouling Compound

In one or more embodiments, the antifouling compound may be present in different isomer states, one such example depicted in Chemical Structure #6. An isomer is an example of a derivative structure of an antifouling compound. For example, and as depicted in Chemical Structure #6, the central aluminum atom of an antifouling compound may be bonded to two oxygen atoms of a single antifouling group to form a chelate ring. It should be understood that while Chemical Structure #6 depicts an isomer where the two oxygen atoms nearest to the central aluminum atom are bonded with the central aluminum atom, in other embodiments other isomers may form, such as an isomer formed when the central aluminum atom forms a bond with an oxygen atom which is not as close as another oxygen atom to the central aluminum atom in the antifouling compound molecule. For example, while Chemical Structure #6 shows a ring structure with two oxygen atoms and n carbon atoms, larger ring structures may form in other isomers, such as rings having three or more oxygen atoms. It should be understood that isomers of the antifouling compound described, such as that shown in Chemical Structure #6, are considered antifouling compound and fit into the base structure depicted in Chemical Structure #1. For instance, the existence of two oxygen atoms bonded to the central aluminum atom, where both oxygen atoms are part of an antifouling group, is considered to conform to the base structure depicted in Chemical Structure #1.

Chemical Structure #6

Example of Isomer of Antifouling Compound

Each of Chemical Structures #3 through #6 illustrates the antifouling compound with the antifouling group of Chemical Structure #2. It will be appreciated that in various embodiments, other or additional antifouling groups may be bonded at R1, R2, or R3 to the central aluminum atom of the generalized antifouling compound of Chemical Structure #1. Specific, non-limiting, additional examples for the antifouling group include the structures such as —NHR, —OC(O)R, and —OS(O)OR.

Additionally, the antifouling compounds may be aluminum complexes formed by the reactions of AlR1R2R3 (Chemical Structure #1) and an ionic surfactant. The resulting antifouling compounds are structurally as illustrated in Chemical Structure #7, where R4 and X⁺ represent the anionic and cationic parts of an ionic surfactant, respectively.

Chemical Structure #7

Example of Antifouling Compounds

In one or more embodiments, the antifouling catalyst system comprises one or more phosphonium antifouling agent. The phosphonium antifouling agent may be combined with the aluminum alkyl compound to form the antifouling compound depicted in Chemical Structure #7. As used in this disclosure, phosphonium antifouling agents include any compound comprising the phosphonium structure depicted in Chemical Structure #8, where $R_1$, $R_2$, $R_3$, and $R_4$ represents chemical groups which may contain other moieties, and the various R groups may be identical or different from one another. Generally, phosphonium antifouling agents may be introduced into the antifouling catalyst system as phosphonium salts, where the phosphonium cation forms an ionic bond with an anion compound. As used in this disclosure, phosphonium antifouling agents include phosphonium salts or zwitterionic compounds comprising phosphonium moieties.

Chemical Structure #8

Generalized Phosphonium Cation

Suitable phosphonium antifouling agents include, without limitation, tetraalkyl phosphonium salts. For example, the antifouling agent may include tetraalkyl phosphonium halides (such as tetrabutyl phosphonium halide), phosphonium malonates (such as tetrabutylphosphonium malonate), trihexyltetradecylphsophonium halides (such as trihexyltetradecylphsophonium bromide), tetrabutylphosphonium halides (such as tetrabutylphosphonium iodide), tetrabutylphosphonium tetrahaloborates (such as tetrabutylphosphonium tetrafluoroborate), tetrabutylphosphonium halides (such as tetrabutylphosphonium chloride), tetrabutylphosphonium hexahalophosphates (such as tetrabutylphosphonium hexafluorophosphate), or tetrabutylphosphonium tetrahaloborates (such as tetrabutylphosphonium tetrafluoroborate). As used throughout this disclosure, a halide may include fluoride, chloride, bromide, or iodide (and "halo" may include the elements fluorine, chlorine, bromine, or iodine). In one or more embodiments, the R groups, that is, $R_1$, $R_2$, $R_3$, and $R_4$, may be linear, branched, or cyclic alkyls, alkenyls, alkynyls, or aryls, and the R groups may be identical or different from one another.

In one or more embodiments, the antifouling catalyst system comprises one or more sulfonate antifouling agents. The sulfonate antifouling agent may be combined with the aluminum alkyl compound to form the antifouling compound depicted in Chemical Structure #7. As used in this disclosure, sulfonate antifouling agents include any compound comprising the structure depicted in Chemical Structure #9, where R represents a chemical group which may contain other moieties. Generally, sulfonate antifouling agents may be introduced into the antifouling catalyst system as a sulfonate salt, where the sulfonate anion forms an ionic bond with a cation compound. As used in this disclosure, sulfonate antifouling agents include sulfonate salts or zwitterionic compounds comprising sulfonate moieties.

Chemical Structure #9

Generalized Sulfonate Anion

Suitable sulfonate antifouling agents include, without limitation, sulfonate salts. For example, sulfonate antifouling agents may include, without limitation, sodium dodecylbenzenesulfonate, sodium dioctylsulfonsuccinate, tetrabutylphosphonium methane sulfonate, tetrabutylphosphonium p-toluenesulfonate, and (hexadecyl) trimethylammonium p-toluenesulfonate. In other embodiments, suitable antifouling agents may include non-salt sulfonates, that is, zwitterionic sulfonates which do not dissociate into a separated cation and anion. For example, non-salt sulfonates suitable as antifouling agents include, without limitation, 3-(dimethyl(octadecyl)ammonio)propane-1-sulfonate, 3,3'-(1,4-didodecylpiperazine-1,4-diium-1,4-diyl)bis(propane-1-sulfonate), and 3-(4-(tert-butyl)pyridinio)-1-propanesulfonate.

In one or more embodiments, the antifouling catalyst system comprises one or more sulfonium antifouling agents. The sulfonium antifouling agent may be combined with the aluminum alkyl compound to form the antifouling compound depicted in Chemical Structure #7. Sulfonium antifouling agents are generally depicted in Chemical Structure #10, where $R_1$, $R_2$, and $R_3$ represent chemical groups which may contain other moieties, and the various R groups, that is, $R_1$, $R_2$, and $R_3$, may be identical or different from one another. Generally, sulfonium antifouling agents may be introduced into the antifouling catalyst system as sulfonium sans, where the sulfonium cation forms an ionic bond with an anion compound. As used in this disclosure, sulfonium antifouling agents include sulfonium salts or zwitterionic compounds comprising sulfonium moieties.

Chemical Structure #10

Generalized Sulfonium Cation

In one or more embodiments, the antifouling catalyst systems may comprise more than one molecular species of antifouling compound. For example, some antifouling compounds may comprise one, two or three antifouling groups, while others comprise a different number of antifouling groups. The mixture of these antifouling compound species may form a bulk antifouling compound which can be characterized by its bulk molar ratio of hydrocarbyl groups to antifouling groups which are attached to the central aluminum atoms, respectively. For example, if half of the antifouling compound has one antifouling group and two hydrocarbyl groups, and, the other half of the antifouling compound has two antifouling groups and one hydrocarbyl group, then the bulk molar ratio of hydrocarbyl groups to antifouling groups would be 1:1 because there is a bulk equal amount of hydrocarbyl groups to antifouling groups. In various embodiments, the bulk molar ratio of hydrocarbyl groups to antifouling groups may be from be from 1:3 to 2:1, 1:2 to 2:1, or from 1:1 to 2:1.

In one or more embodiments, the antifouling catalyst system may comprise one or more ether compounds to reduce the formation of polymers. The one or more ether compounds may include cyclic ethers such as, but not limited to, tetrahydrofuran (THF), 1,4-dioxane, tetrahydropyran (THP), or combinations thereof.

The antifouling catalyst systems may comprise at least one or more titanate compounds, one or more aluminum alkyl compounds, and one or more antifouling compounds. In various embodiments, the molar ratio of total titanate compounds to total aluminum alkyl compounds may be from 1.5 to 3.0, or from 2.0 to 3.0.

In various embodiments, the molar ratio of the antifouling agents brought into contact with the aluminum alkyl compound to the sum of the aluminum alkyl compounds brought into contact with the aluminum alkyl compound and additionally provided into the reactor may be from 0.001:1 to 0.5:1, from 0.01 to 0.18, or from 0.01 to 0.13.

In various embodiments, the molar ratio of total titanate compounds to total ether compounds may be from 120 to 1:0, from 1:10 to 1:1, or from 1:8 to 1:3.

It should be understood that the molar ratios of components of the antifouling catalyst systems described previously are representative of the total amount of each component of the antifouling catalyst system relative to the total amount of titanate compound or aluminum alkyl compound, where the "total" amount refers to the molar amount of all species of the antifouling catalyst system which may be considered as a particular component type, that is, titanate compound, aluminum alkyl compound, ether compound, or antifouling agent. The total amount of a component may include two or more chemical species which are titanate compounds, aluminum alkyl compounds, ether compounds, or antifouling agents, respectively.

In one or more embodiments, without being bound by theory, it is believed that heteroatoms such as oxygen or nitrogen of the antifouling compounds may form weak coordination with the titanate compound utilized as the catalyst in the catalyst system. It is believed that, in one or more embodiments, the alkyl groups or other relatively long-chained groups of the antifouling compounds may serve in some capacity to prevent ethylene access to the catalytic center of the titanate compound. The restriction of access of the ethylene to the titanate catalytic site may reduce the polymerization of ethylene and thus reduce reactor fouling.

In one or more embodiments, the introduction of the antifouling compound into the catalyst system may suppress polymer formation while not greatly reducing catalytic activity of 1-butene formation. In one embodiment, polymer formation (fouling) may be reduced by at least 5%, 10%, 20%, 30%, 40%, 50%, 60%, 70%, 80%, 90%, or even 95% by the inclusion of an antifouling compound. In one embodiment, 1-butene production may be increased, stay the same, or may decrease by less than or equal to 50%, 40%, 30%, 20%, 10% or even 5% by the inclusion of an antifouling compound. In some embodiments, antifouling compounds may both reduce the polymer formation, such as by at least 5%, 10%, 20%, 30%, 40%, 50%, 60%, 70%, 80%, 90% or even 95%, and increase, not effect, or decrease 1-butene production rate by less than or equal to 50%, 40%, 30%, 20%, 10% or even 5%. Reduction in polymer formation rates and catalytic activity on a percentage basis are based on catalyst systems which include one or more antifouling compounds described as compared with catalyst systems which are void of an antifouling compound.

EXAMPLES

The various embodiments of antifouling catalyst systems and the performance of the antifouling compound injection system will be further clarified by the following examples. The examples are illustrative in nature, and should not be understood to limit the subject matter of the present disclosure.

The Antifouling Catalyst System

To evaluate the antifouling effects of the antifouling catalyst systems and processes described, ethylene dimerization reactions were carried out and evaluated. Multiple sample antifouling catalyst systems were formulated and tested in accordance with the processes of this disclosure. The process for selective ethylene dimerization with antifouling components and the associated antifouling compound injection system were compared to baseline comparative systems. Specifically, with the antifouling compound injection system, the co-catalyst and the antifouling agent were premixed in the antifouling compound mixing vessel before injection into the process reactor as a separate stream from the catalyst. For testing, $(CH_3CH_2)_2AlO(C_2H_4O)_4(CH_2)_{11}CH_3$ (Chemical Structure #4) was utilized as the antifouling compound. Specifically, for the experiments, tetrabutyl orthotitanate (denoted as "Ti" in Table 1) in tetrahydrofuran (1:6) as the catalyst, triethyl aluminum (TEAL) as the co-catalyst, and $C_{12}H_{25}(OC_2H_4)_4OH$ as the antifouling agent were used. The antifouling agent $C_{12}H_{25}(OC_2H_4)_4OH$, triethylaluminum, and tetrabutyl orthotitinate in tetrahydrofuran are referred below as A, B, and C, respectively. Tables 1 and 2 show the dimerization activity and selectivity of polymer for continuous reactions which utilized catalyst systems with varying combinations of A, B, and C. For these continuous reactions, a 5 L reactor was first charged with 1160 g of 1-butene. Then, the reactor was heated to 53° C. and pressurized with ethylene to 2.3 MPa. Separately, the antifouling agent A was added to the hexane solution of triethylaluminum B to prepare an antifouling compound solution with the Al concentration of 0.053 mol/L. After that, continuous feed of the 0.018 mol-Ti/L hexane solution of C (6.2 mL/h) and the premixed solution of A and B (4.6-7.0 mL/h) was started via separate lines to begin the reaction. The reaction was continued for 30 hours with the reactor stirred at the rate of 400 rpm. During the reaction, the liquid in the reactor was continuously discharged via a dip tube to maintain the liquid level and to keep the catalyst residence time at 7 hours. Table 1 accounts for premixing and utilization of the antifouling compound, and Table 3 accounts for experiments without the antifouling agent A. As is evident by the reaction data of Tables 1 and 2 the addition of the premixing step in the antifouling compound mixing vessel greatly reduced polymer formation and/or increased the ease in removing any polymer formed, which was quantified in accordance with a subjective scale. In which a 4 represents removable by rubbing with a cloth softly, a 3 represents removable by rubbing with a cloth strongly, a 2 represents removable by brushing with a steel wool, and a 1 represents hard to remove by brushing with a steel wool. As indicated by Tables 1 and 2, the addition of the premixing step in the antifouling compound mixing vessel also greatly increased the ease in removing any polymer formations as evidenced by higher polymer removability ratings. However, it should be noted that the use of a large amount of the antifouling agent causes decrease in activity or increase in polymer selectivity, and it is thus preferable that the molar ratio of the antifouling agent to the aluminum alkyl compound is within a suitable range.

TABLE 1

| | B/Ti (mol/mol) | A/B (mol/mol) | Activity (kilograms of ethylene per moles of titanium) kg-$C_2$/mol-Ti | Polymer Selectivity (wt ppm) | Polymer Removability* |
|---|---|---|---|---|---|
| Example #1 | 2.47 | 0.02 | 867 | 31 | 3 |
| Example #2 | 2.28 | 0.04 | 717 | 30 | 4 |
| Example #3 | 2.60 | 0.04 | 1096 | 72 | 4 |
| Example #4 | 2.61 | 0.04 | 934 | 96 | 4 |
| Example #5 | 2.78 | 0.04 | 1121 | 60 | 4 |
| Example #6 | 2.28 | 0.08 | 572 | 28 | 4 |
| Example #7 | 2.51 | 0.08 | 756 | 31 | 4 |
| Example #8 | 2.91 | 0.08 | 1076 | 99 | 4 |
| Example #9 | 2.98 | 0.08 | 1238 | 157 | 4 |
| Example #10 | 2.79 | 0.12 | 923 | 131 | 4 |
| Example #11 | 2.90 | 0.16 | 940 | 110 | 3 |
| Example #12 | 2.99 | 0.21 | 415 | 1727 | 4 |

TABLE 2

| | B/C (mol/mol) | A/B (mol/mol) | Activity (kilograms of ethylene per moles of titanium) kg-$C_2$/mol-Ti | Polymer Selectivity (wt ppm) | Polymer Removability* |
|---|---|---|---|---|---|
| Comparative Example #1 | 2.44 | 0 | 1117 | 119 | 2 |
| Comparative Example #2 | 2.48 | 0 | 998 | 126 | 1 |
| Comparative Example #3 | 2.58 | 0 | 1009 | 228 | 1 |
| Comparative Example #4 | 2.60 | 0 | 1125 | 200 | 1 |
| Comparative Example #5 | 2.81 | 0 | 1098 | 196 | 1 |
| Comparative Example #6 | 3.07 | 0 | 1267 | 320 | 1 |
| Comparative Example #7 | 3.11 | 0.04 | 1423 | 265 | 2 |
| Comparative Example #8 | 3.42 | 0.08 | 1630 | 303 | 3 |

In addition, similar continuous reactions in which the stream of the catalyst component B, which had been premixed with A when applied, and the stream of the catalyst component C were combined and fed to a reactor as a single stream. Catalyst residence time from the combined point to the injection point was about 1 hour. The other conditions are the same as those described above. The results are listed in Table 3, showing that the addition of the premixing step in the antifouling compound mixing vessel can cause the increase in the polymer formation rather than decrease when the feed streams are combined. These data suggest that the contact of the components C and premixed A/B before injection should be avoided, and it is preferable to inject the two components as separate streams.

TABLE 3

| | TEAL/TBT (mol/mol) | Brij L4/TEAL (mol/mol) | Activity (kg-$C_2$/mol-Ti) | Polymer selectivity (wt ppm) |
|---|---|---|---|---|
| Comparative Example #9 | 2.66 | 0 | 761 | 227 |
| Comparative Example #10 | 2.42 | 0 | 749 | 306 |
| Comparative Example #11 | 2.52 | 0.12 | 745 | 461 |
| Comparative Example #12 | 2.73 | 0.12 | 1177 | 288 |

To simulate the effect of the antifouling compound on the thermal conductivity degradation of heat exchangers in commercial ethylene dimerization processes, the time courses of the overall heat transfer coefficients of the reactor observed in Comparative Example #4 and with Example #5 were extrapolated to 4 weeks later as shown in Table 4.

TABLE 4

| | Overall Heat Transfer Coefficient (kcal/(h · $m^2$ · K)) | |
|---|---|---|
| Week | Example #5 | Comparative Example #4 |
| 0 | 600 | 600 |
| 1 | 556 | 471 |
| 2 | 515 | 370 |
| 3 | 477 | 290 |
| 4 | 443 | 228 |

The results shown in Table 4 indicate that the addition of the antifouling compound with the antifouling compound injection system results in the slower degradation of the heat exchanger conductivity, which means the heat exchanger is able to remain online and be operated for an extended period of time.

The Jet Loop Reactor

Figure 5A:
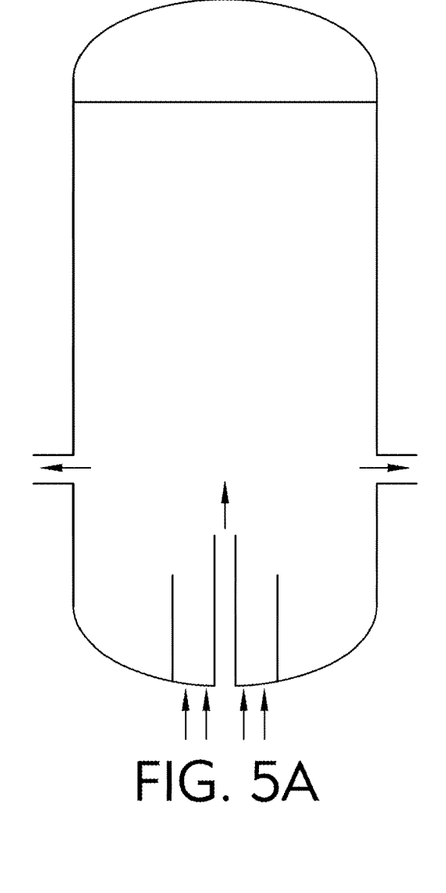
FIG. 5A is a schematic illustration of a comparative loop reactor.
Figures 5B, 5C:
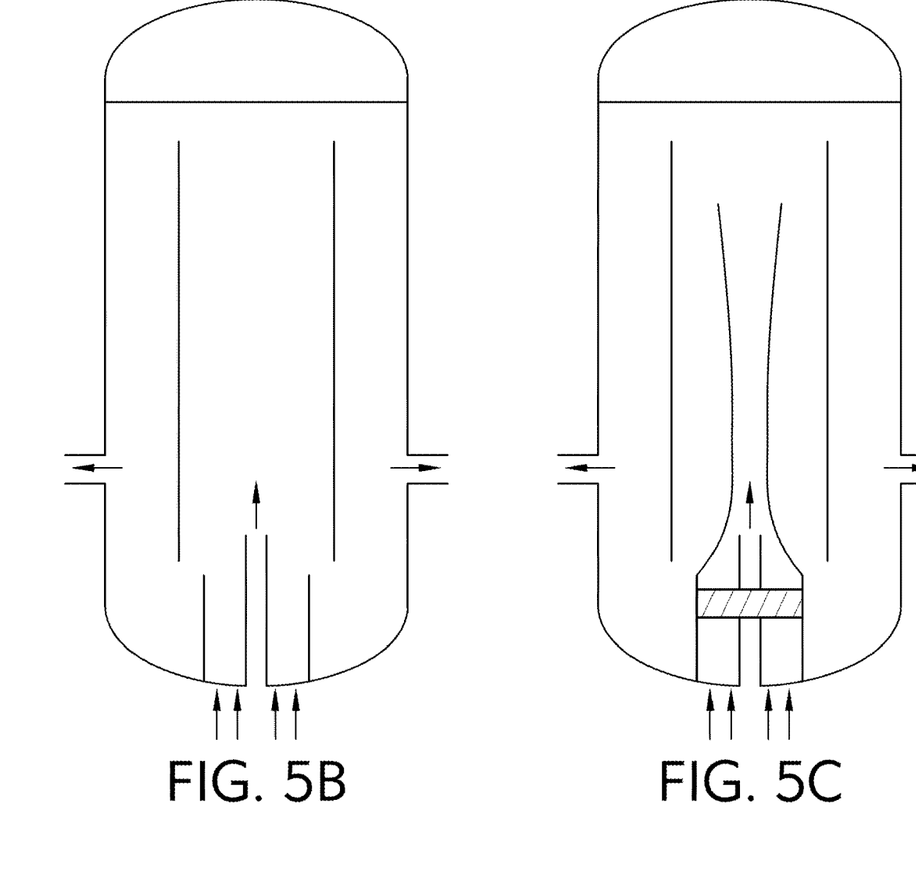
FIG. 5B is a schematic illustration of a comparative loop reactor.
FIG. 5C is a schematic illustration of a generalized jet loop reactor in accordance with one or more embodiments of the present disclosure.

The reaction was carried using the reactors depicted in FIG. 5A-5C, which operated in an upflow configuration. The reactions were carried out at a temperature of about 120° C., a pressure of about 50 Kg/$cm^2$, and a feed comprising ethylene.

FIG. 5A depicts an upflow reactor with a co-axial nozzle and draft tube. It should be understood that as the co-axial nozzle of FIGS. 5A and 5B lack a Venturi geometry, they are not jet nozzles as described in the present application. FIG. 5C depicts an upflow jet loop reactor where the jet nozzle is a closed jet nozzle with vanes. The results of these reactors are described in Table 5. In Table 5, the amount of polymer and 1-hexene are normalized to the quantities of these materials produced in the upflow jet loop reactor of FIG. 5C where the jet nozzle is a closed jet nozzle with vanes.

TABLE 5

| | Co-Axial Nozzle Without Draft Tube (FIG. 5A) | Co-Axial Nozzle With Draft Tube (FIG. 5B) | Closed Nozzle with Vanes and Draft Tube (FIG. 5C) |
|---|---|---|---|
| Decene | 0.000163 | 0.000570 | 0.035058 |
| Hexene | 0.041925 | 0.108449 | 0.347967 |
| 6-Dodecene | 0.000005 | 0.000033 | 0.015083 |
| Ethylene | 0.262271 | 0.442070 | 0.162492 |
| Heptane | 0.441716 | 0.445344 | 0.435326 |
| Polymer | 2.73E–07 | 3.46E–07 | 1.92E–07 |
| Hexene | 0.001397 | 0.003533 | 0.004024 |
| Heptane | 0.252523 | 0.000001 | 0.000050 |
| Total m.f. | 0.747477 | 0.999999 | 0.999950 |
| Conversion (ethylene) | 0.14223 | 0.20298 | 0.71221 |
| Selectivity (1-hexene) | 0.96402 | 0.96326 | 0.86530 |
| Yield (1-hexene) | 0.13712 | 0.19552 | 0.61628 |
| Relative Yield (1-Hexene) | 22% | 32% | 100% |
| Selectivity (polymer) | 6.27E–06 | 3.07E–06 | 4.76E–07 |
| Yield (polymer) | 8.92E–07 | 6.23E–07 | 3.39E–07 |
| Relative Yield (polymer) | 263% | 184% | 100% |

As can be seen in Table 5, the examples (FIGS. 5A and 5B) without the jet nozzle produced one third or less hexene than the example with the jet nozzle and draft tube (FIG. 5C). Additionally, the examples without the jet nozzle produced nearly twice as much polymeric waste product than the example with the jet nozzle.

What is claimed is:

1. A process for the oligomerization of ethylene, the process comprising: contacting ethylene, a catalyst system, and an antifouling compound in a jet loop reactor, thereby oligomerizing ethylene and producing a product stream comprising one or more of 1-butene, 1-hexene, or 1-octene.

2. The process for the oligomerization of claim 1, wherein the antifouling compound comprises the structure:

or its dimeric form wherein one or more of the chemical groups R1, R2, and R3 are the antifouling agent comprising the structure —O((CH$_2$)$_n$O)$_m$R4, wherein n is an integer of from 1 to 20, m is an integer of from 1 to 100, and R4 is a hydrocarbyl group, and wherein the chemical groups R1, R2, or R3 that do not comprise the antifouling agent, if any, are hydrocarbyl groups.

3. A process for selectively producing oligomers, the process comprising:
bringing at least one antifouling agent into contact with a first amount of at least one aluminum alkyl compound to form at least one antifouling compound comprising the structure:

or its dimeric form wherein one or more of the chemical groups R1, R2, and R3 are the antifouling agent comprising the structure —O((CH$_2$)$_n$O)$_m$R4, wherein n is an integer of from 1 to 20, m is an integer of from 1 to 100, and R4 is a hydrocarbyl group, and wherein the chemical groups R1, R2, or R3 that do not comprise the antifouling agent, if any, are hydrocarbyl groups; and feeding the at least one antifouling compound, an additional amount of the at least one aluminum alkyl compound, at least one titanate compound, and ethylene into a jet loop reactor and oligomerizing ethylene to produce one or more of 1-butene, 1-hexene, or 1-octene;
wherein the at least one titanate compound is fed as a stream separate from the streams of the at least one antifouling compound and the additional amount of the at least one aluminum alkyl compound, and
wherein the of the sum of the first amount and the additional amount of the at least one aluminum alkyl compound to the at least one titanate compound is equal to or higher than 1.5 and equal to or lower than 3.0.

4. The process of claim 3, wherein the jet loop reactor comprises a jet nozzle.

5. The process of claim 3, wherein the jet loop reactor comprises a jet nozzle comprising a Venturi geometry.

6. The process of claim 3, wherein the jet nozzle is a pre-mixed open jet nozzle or a closed jet nozzle.

7. The process of claim 6, wherein the jet nozzle is a closed jet nozzle and the closed jet nozzle comprises vanes.

8. The process of claim 3, wherein
the jet loop reactor comprises a jet nozzle comprising a narrowing section, a throat section, and a diverging section;
the jet loop reactor comprises a draft tube disposed within a body of the jet loop reactor; and
the diverging section is disposed within the draft tube.

9. The process of claim 8, wherein the jet loop reactor further comprises a deflector plate disposed within a direction of flow of ethylene exiting the jet nozzle.

10. The process of claim 3, wherein the jet loop reactor does not include a mechanical agitator.

11. The process of claim 3, wherein ethylene comprises carbon atoms and the carbon atoms have a normalized exit age ($E_\theta$) of greater than or equal to 0.2 at 200 seconds and Ee of greater than or equal to 0.4 at 100 seconds, where Ee is determined according to the equation $$E_\theta = e^{-\theta} \text{ and } \theta = \frac{t}{t^1}.$$

12. The process of claim 3, wherein the oligomerizing ethylene produces 1-butene.

13. The process of claim 3, wherein the oligomerizing ethylene produces less than 1 wt. % of polymer, on the basis of the total amount of ethylene fed to the jet loop reactor.

14. The process of claim 3, wherein:
the first amount of the at least one antifouling agent is brought into contact with an excess amount of the at least one aluminum alkyl compound to form an antifouling mixture comprising the at least one antifouling compound and the remainder of the first amount of the at least one aluminum alkyl compound, and
the antifouling mixture, the at least one titanate compound, and ethylene are fed into the reactor.

15. The process of claim 3, wherein the molar ratio of the antifouling agents brought into contact with the aluminum alkyl compound to the sum of the aluminum alkyl compounds brought into contact with the aluminum alkyl compound and the aluminum alkyl compounds additionally provided into the reactor is equal to or greater than 0.01 and equal to or lesser than 0.18.

16. The process of claim 3, wherein n is from 1 to 5.

17. The process of claim 3, wherein m is from 1 to 20.

18. The process of claim 3, wherein R4 has from 1 to 100 carbon atoms.

19. The process of claim 3, an atom existing in the chemical groups R1, R2, or R3 binds to the aluminum atom to form a chelate ring.

* * * * *